(12) United States Patent
Pinkos et al.

(10) Patent No.: US 8,466,299 B2
(45) Date of Patent: Jun. 18, 2013

(54) PROCESS FOR PREPARING DELTA-VALEROLACTONE IN THE GAS PHASE

(75) Inventors: Rolf Pinkos, Bad Duerkheim (DE); Christophe Bauduin, Plankstadt (DE); Axel Paul, Lampertheim (DE); Gerhard Fritz, Dannstadt-Schauernheim (DE); Hans Wagner, Gruenstadt (DE)

(73) Assignee: BASF SE, Ludwigshafen (DE)

( * ) Notice: Subject to any disclaimer, the term of this patent is extended or adjusted under 35 U.S.C. 154(b) by 77 days.

(21) Appl. No.: 13/131,310

(22) PCT Filed: Dec. 2, 2009

(86) PCT No.: PCT/EP2009/066186
§ 371 (c)(1),
(2), (4) Date: May 26, 2011

(87) PCT Pub. No.: WO2010/063742
PCT Pub. Date: Jun. 10, 2010

(65) Prior Publication Data
US 2011/0237806 A1    Sep. 29, 2011

(30) Foreign Application Priority Data

Dec. 5, 2008   (EP) .................................... 08170862

(51) Int. Cl.
*C07D 309/00*         (2006.01)

(52) U.S. Cl.
USPC .......................................... 549/273

(58) Field of Classification Search
USPC .......................................... 549/273
See application file for complete search history.

(56) References Cited

U.S. PATENT DOCUMENTS

| | | |
|---|---|---|
| 5,106,995 A | 4/1992 | Plotkin |
| 2010/0168445 A1 | 7/2010 | Pinkos et al. |
| 2010/0240913 A1 | 9/2010 | Pinkos et al. |
| 2010/0256398 A1 | 10/2010 | Pinkos et al. |

FOREIGN PATENT DOCUMENTS

| | | |
|---|---|---|
| CN | 101 157 677 | 4/2008 |
| EP | 1 214 972 | 6/2002 |
| GB | 583 344 | 12/1946 |
| JP | 04 261167 | 9/1992 |
| JP | 2004 331626 | 11/2004 |
| WO | 90 14344 | 11/1990 |

*Primary Examiner* — Nizal Chandrakumar
(74) *Attorney, Agent, or Firm* — Oblon, Spivak, McClelland, Maier & Neustadt, L.L.P.

(57) ABSTRACT

The process relates to a process for preparing delta-valerolactone (VLO) in the gas phase by catalytic dehydrogenation over at least two different catalysts.

14 Claims, No Drawings

PROCESS FOR PREPARING DELTA-VALEROLACTONE IN THE GAS PHASE

The process relates to a process for preparing delta-valerolactone (VLO) in the gas phase by catalytic dehydrogenation over at least two different catalysts.

VLO is a sought-after starting material for preparing cyclic lactams, as an intermediate for polylactones and for producing pharmaceuticals or crop protection compositions.

EP-A 1214972 describes the preparation of gamma-butyrolactone in the gas phase from 1,4-butanediol. In general, this disclosure also includes the teaching that VLO can be prepared from the corresponding pentanediol. The use of at least two catalysts arranged in layers for this reaction is, however, not disclosed. Only few experiments and experimental conditions for controlled preparation of VLO from 1,5-pentanediol are known from the prior art.

JP 2004331626 mentions, in an example, that VLO can be prepared in the gas phase over a copper oxide/silica catalyst which was kept at 260° C. A reaction discharge which comprised 85% by weight of VLO was obtained. The use of two different catalysts to prepare VLO is not described here.

The conversion of a diol to the corresponding lactone with elimination of hydrogen and exclusion of oxygen is an endothermic reaction. To achieve high conversions, heat therefore has to be supplied to the system. The distances between the hot zones must therefore not be too long, otherwise there is undesired cooling of the gas stream and hence low conversion. Moreover, the high-boiling diol can condense on the catalyst, which generally leads to short service life or lifetime of the catalyst, for example as a result of coking. In technical terms, heat is supplied by means of a tube bundle reactor in which catalyst-conducting tubes with diameters of, for example, 3 cm run through a heating medium such as a salt bath or steam for introduction of heat. Tube bundle reactors are, however, complex in terms of management and very expensive. This also applies to reactors which are constructed like a shaft reactor but have a large number of installed pipe coils or heat exchanger plates, in order that sufficient energy can be supplied.

It is therefore an object of the present invention to provide a process for preparing delta-valerolactone with a purity of >98%, in which it is possible to use a reactor in which only the amount of heat required to heat the feed streams need be introduced upstream of the reactor. The use even of technically noncomplex reactors such as shaft reactors without further internals would thus be possible. It is a further object of the invention to lower the proportion of secondary components, especially those which lead to chain terminations in polymerization applications, or components which lower the color number stability, such as aldehydic components.

The object is achieved by a process for preparing delta-valerolactone proceeding from 1,5-pentanediol in the gas phase, comprising the following steps:
a) evaporating the 1,5-pentanediol in an inert gas stream
b) passing the inert gas stream comprising 1,5-pentanediol through the catalyst bed comprising at least two different catalysts
c) condensing reaction product out of the gas mixture obtained from step b), wherein the catalysts used comprise the elements and/or compounds of the elements of periods 7 to 12 of the Periodic Table and have a layer structure such that the inert gas stream comprising 1,5-pentanediol flows first through the catalyst which exhibits the highest conversions and selectivities for the preparation of delta-valerolactone proceeding from 1,5-pentanediol at the given catalyst bed inlet temperature, and then through the catalyst which exhibits the highest conversions and selectivities for the preparation of delta-valerolactone proceeding from 1,5-pentanediol at lower temperatures.

It has now been found that, surprisingly, VLO can be prepared particularly advantageously by passing 1,5-pentanediol in the gas phase together with an inert gas over at least two catalysts, said catalysts catalyzing the reaction optimally at different temperatures.

In the case of use of only a single catalyst, as the comparative example shows, either the reactivity or the selectivity is nonoptimal, unless further heat supply takes place during the reaction. For instance, in the case of use of only one catalyst which has its highest reactivity and selectivity at a particular temperature, the starting temperature is lowered owing to the endothermic reaction enthalpy to such an extent that conversion losses occur. When, in contrast, in the case of such a system which works only with one catalyst, the starting temperature is increased above the optimal temperature, a higher conversion is achieved, but the selectivity of the catalyst falls, which can also lead to short catalyst service lives.

In the process according to the invention, the temperatures are higher at the catalyst bed inlet than at the catalyst bed outlet. The temperature at the catalyst bed inlet is preferably in the range from 260 to 350° C., more preferably in the range from 270 to 330° C. At the catalyst bed outlet, the temperature is preferably in the range from 180 to 240° C., more preferably in the range from 190 to 230° C.

The carrier gas used for the reaction is an inert gas. This inert carrier gas is preferably selected from the group of hydrogen, nitrogen, argon and methane. Particular preference is given to hydrogen. The molar ratio of 1,5-pentanediol to inert gas based on the reactor inlet may be between 1:0.1 and 300. Preference is given, however, to performance with an inert carrier gas in a ratio of 1,5-pentanediol to inert gas of 1:0.5 to 200, more preferably of 1:2 to 150.

The pressure in steps a) to c) of the process according to the invention is preferably adjusted such that no liquid phase forms in the reactor. The pressure is more preferably between 0.5 and 10 bar absolute, most preferably between 1 and 5 bar absolute.

The catalysts used in the process according to the invention are those which comprise elements and/or compounds of the elements of groups 7 to 12 of the Periodic Table.

The inventive catalysts may comprise oxidic catalysts, preference being given to those which are typically used for dehydrogenation reactions, for example the dehydrogenation of cyclohexanol to cyclohexanone. These transition metal elements of groups 7 to 12 of the Periodic Table may be present in elemental form or at least partly in oxidic form. Preferred transition metal elements are selected from the group of Zn, Ag, Cu, Ru and Au, particular preference being given to Cu. For the purposes of fine control of the catalyst properties, further elements may also be present as dopants. These dopants are, for example, basic components, such as oxides, hydroxides or carboxylates of the elements of groups 1-14. Preference is given to basic components of the alkali metal elements and alkaline earth metal elements.

The transition metal elements are applied to oxidic support materials or activated carbons. Preferred support materials are activated carbons and oxides of Al, Si, Zn, Ti, Fe, Cr, Zr. There can also be mixtures of the individual oxides or mixed compounds, as occur in zeolites and aluminas.

The contents of the transition metal elements on the supports are between 3 and 97% by weight, preference being given to 5 to 80% by weight and particular preference to 10 to 70% by weight.

The catalysts can be activated before installation into the reactor, or else in situ in the reactor. When the catalysts are activated before installation, it is advantageous when they are passivated after activation, in particular when the active component is to be present in metallic form. It is also possible to use the activated catalysts for installation without passivation, and for that purpose in an inert solvent such as pentanediol.

In the process according to the invention, the delta-valerolactone is prepared by converting 1,5-pentanediol over at least two catalyst layers in series. For the process according to the invention, it is also possible to insert further layers of other catalysts upstream of, between or downstream of the two layers. A prerequisite for a catalyst bed comprising two or else more than two layers is, however, that the layers within the catalyst bed have a structure such that the inert gas stream comprising 1,5-pentanediol flows first through the catalyst which exhibits the highest conversions and selectivities for the conversion of 1,5-pentanediol to delta-valerolactone at the highest temperature, followed by all further catalyst layers which exhibit the highest conversions and selectivities for the inventive conversion at constantly falling temperatures. For the process according to the invention, it is essential that the catalyst bed which comprises at least two different catalysts is structured in layers which do not mix.

In the inventive step c), the gas stream from the reactor is cooled such that the reaction components which are liquid under standard conditions are at least substantially condensed out. This can be done by conventional heat exchangers, but it is in principle also or additionally possible to scrub these components out with a substance which is already liquid. Preference is given to using the liquid reaction product itself for scrubbing.

After the inventive step c), a portion of the inert gas, for example that formed during the reaction, can be discharged from the process in a further step, d). The remainder can be fed back to the process according to the invention in step a). This is preferably achieved by a cycle gas blower.

The liquid constituents thus obtained in step c) can be subjected to a distillative or rectificative workup in a further step, e). In this case, any 1,5-pentanediol present after removal in step a) of the process according to the invention can be recycled, and pure valerolactone can be obtained. The purities of the valerolactone are more than 98%, preferably more than 99%.

EXAMPLES

The process according to the invention is illustrated in detail, but not limited, by means of the examples which follow. The gas chromatography (GC) percentages reported in the examples are area percentages (area %).

Example 1

Inventive

A tubular reactor with an internal diameter of 32 mm and an outer jacket which is there to prevent heat losses from the reactor was charged, in a first layer, with 25 ml of a copper catalyst (catalyst 1, 5×3 mm tablets, 21% copper oxide, 2% sodium oxide, remainder $SiO_2$, prepared by impregnating ammoniacal copper carbonate/sodium nitrate solution onto $SiO_2$ extrudates, followed by drying and calcination) and with a second layer below it of 25 ml of a second copper catalyst (catalyst 2, 5 mm extrudates, 13% copper oxide, 1% sodium oxide, 7% CaO, remainder $SiO_2$, prepared by impregnation of ammoniacal copper carbonate/sodium nitrate solution onto $CaO/SiO_2$ extrudates, followed by drying and calcination). Above the tubular reactor there was a heating zone which was used as an evaporator and by means of which the reactor inlet temperature was variable.

By means of a nitrogen/hydrogen mixture of 10 to 1 (10 standard liters/h), the catalysts were activated up to 180° C. within 72 h.

By means of a pump, thereafter, 1,5-pentanediol (purity 97%, approx. 4 g/h) and hydrogen (10 standard liters/h) were metered in via the evaporator at standard pressure. The temperature at the reactor inlet was set to 300° C. A thermometer at the start of the second catalyst layer measured approx. 260° C. The discharge was cooled to approx. 10° C.; the liquid obtained was collected; the gas was discharged. The reaction was conducted over a period of 700 h, then stopped. After 24 h and even after 700 h, the 1,5-pentanediol conversion was more than 99%. The VLO content in the liquid discharge over this period was between 93 and 94%; the 5-hydroxypentanal intermediate was always significantly below 0.2%. The valerolactone selectivity was accordingly between 96 and 97%.

Some of the liquid reaction effluents were distilled. It was possible to achieve VLO purities of more than 99%.

Example 2

Comparative Example

Example 1 was repeated, with the difference that, instead of catalyst 2, an additional 25 ml of catalyst 1 were introduced.

The 1,5-pentanediol conversion was nearly 99% within the first 300 h; the content of the 5-hydroxypentanal intermediate was up to 4%; the VLO content was correspondingly between 90 and 92%. After 300 h, the pentanediol conversion fell continuously and reached only approx. 94% after 580 h. The VLO selectivities reached a maximum of 95%. After 580 h, the test was stopped.

The distillation of the discharges gave VLO purities up to 98%, though intolerably high proportions of 5-hydroxypentanal were present, such that the resulting product did not have a stable color number.

Example 3

Comparative Example

Example 1 was repeated, with the difference that, instead of catalyst 1, 25 ml of catalyst 2 were additionally introduced.

The conversion of 1,5-pentanediol was more than 99% at the start, but the VLO selectivity was less than 90% and the increase in 5-hydroxypentanal and other products rose so significantly that the test had to be stopped as early as after 100 h.

Example 4

Comparative Example

Example 3 was repeated, with the difference that the reactor inlet temperature was 260° C. The conversion of 1,5-pentanediol was only approx. 85%, and so this test was likewise stopped after 100 h.

The catalyst of comparative Example 4 possesses an optimal reactivity coupled with optimal selectivity between 230 and 250° C. If a gaseous stream consisting of 1,5-pentanediol and hydrogen is now introduced in a ratio relative to one another so as to cause 50° C. of thermal cooling owing to the endothermic reaction enthalpy by the time a maximum conversion is achieved, only approx. 50% of the possible conversion is obtained at a reactor inlet temperature of 250° C. and a reactor outlet temperature of 220-230° C. At increased inlet temperature, for example 280° C., it was possible to achieve sufficient conversion, but at reduced selectivity and also insufficient catalyst lifetime.

The invention claimed is:

1. A process for preparing a delta-valerolactone from 1,5 pentanediol, comprising:
   a) evaporating the 1,5-pentanediol in an inert gas stream wherein the inert gas is selected from the group consisting of hydrogen, nitrogen, argon, and methane;
   b) passing the inert gas stream comprising 1,5-pentanediol through a catalyst bed comprising at least two different copper based catalysts in a layered structure wherein the catalyst bed has an inlet temperature in the range of from 260 to 350° C. and an outlet temperature in a range of from 180 to 240° C., to obtain a gas mixture; and
   (c) condensing a reaction product out of the gas mixture obtained in b)
   wherein the catalysts have a layer structure such that the inert gas stream comprising 1,5-pentanediol flows first through the catalyst which exhibits the highest conversion and selectivity for preparing the delta-valerolactone proceeding from 1,5-pentanediol at a given catalyst bed inlet temperature, and then through the catalyst which exhibits the highest conversion and selectivity for preparing the delta-valerolactone proceeding from 1,5-pentanediol at a lower temperature.

2. The process of claim 1, wherein a ratio of the 1,5-pentanediol to the inert gas is in a range from 1:0.1 to 300.

3. The process of claim 1, wherein the inert gas is hydrogen and a ratio of the 1,5-pentanediol to the hydrogen is in a range from 1:2 to 150.

4. The process of claim 1, wherein the catalysts further comprise at least one transition metal selected from the group consisting of ruthenium, and gold.

5. The process of claim 1, wherein the catalysts further comprise at least one alkali metal oxide.

6. The process of claim 1, wherein at least one of the catalysts is applied to at least one support material selected from the group consisting of activated carbon and an oxide selected from the group consisting of aluminum, silicon, zinc, titanium, iron, chromium, and zirconium, and mixtures of these oxides.

7. The process of claim 1, wherein at least one further catalyst layer is present in at least one location selected from the group consisting of upstream of, between, and downstream of the two catalyst layers at least present in the catalyst bed
   having a structure such that the inert gas stream comprising 1,5-pentanediol flows first through the catalyst layer which exhibits the highest conversion and the highest selectivity for the conversion of 1,5-pentanediol to delta-valerolactone at the catalyst bed inlet temperature, followed by the catalyst layers which exhibit the highest conversions and selectivities for the conversion of 1,5-pentanediol to delta-valerolactone at constantly falling temperature, according to their conversion and selectivity rates.

8. The process of claim 1, carried out at a pressure in a range from 1 to 5 bar absolute.

9. The process of claim 1, wherein a portion of the inert gas obtained from c) is recycled to a) of the process.

10. The process of claim 1, wherein liquid reaction components obtained from c) are subjected to a distillation or rectification.

11. The process of claim 10, wherein unconverted 1,5-pentanediol obtained after the distillation or rectification is recycled to a) of the process.

12. The process of claim 1, wherein a ratio of the 1,5-pentanediol to the inert gas is in a range from 1:0.1 to 300.

13. The process of claim 1, wherein the inert gas is hydrogen and a ratio of the 1,5-pentanediol to the hydrogen is in a range from 1:2 to 150.

14. The process of claim 2, wherein the inert gas is hydrogen and a ratio of the 1,5-pentanediol to the hydrogen is in a range from 1:2 to 150.

\* \* \* \* \*